(12) United States Patent
Denu et al.

(10) Patent No.: US 7,521,432 B2
(45) Date of Patent: Apr. 21, 2009

(54) COMPOSITIONS AND METHODS FOR IDENTIFYING AGENTS WHICH REGULATE CHROMOSOMAL STABILITY, GENE ACTIVATION AND AGING

(75) Inventors: John M. Denu, Tigord, OR (US); Kirk G. Tanner, Westborough, MA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 11/739,973

(22) Filed: Apr. 25, 2007

(65) Prior Publication Data

US 2007/0255045 A1 Nov. 1, 2007

Related U.S. Application Data

(63) Continuation of application No. 10/416,388, filed as application No. PCT/US01/47159 on Nov. 13, 2001, now Pat. No. 7,291,606.

(60) Provisional application No. 60/247,827, filed on Nov. 10, 2000.

(51) Int. Cl.
*A01N 43/04* (2006.01)
*A61K 31/70* (2006.01)

(52) U.S. Cl. .............................. 514/47; 514/45; 514/46; 536/26.1; 536/26.22; 536/26.23; 536/26.24; 536/26.5; 536/26.7; 536/26.71; 424/1.57; 424/1.73; 424/1.77; 424/137.1; 424/141.1; 424/175.1; 424/184.1

(58) Field of Classification Search ........................ None
See application file for complete search history.

(56) References Cited

U.S. PATENT DOCUMENTS 5,658,890 A 8/1997 Pankiewicz et al.

OTHER PUBLICATIONS

Tanner et al., PNAS (Dec. 19, 2000), vol. 97, pp. 14178-14182.

Frye, R.A., "Phylogenetic classification of prokaryotic and eukaryotic Sir2-like proteins", Biochem. Biophys. Res. Commun. vol. 273: pp. 793-798, (2000).

Tsang, A.W., et al., "CobB, a new member of the SIR2 family of eucaryotic regulatory proteins, is required to compensate for the lack of nicotinate mononucleotide:5,6-dimethylbenzimidazole phosphoribosyltransferase activity in cobT mutants during cobalamin biosynthesis in *Salmonella typhimurium* LT2", J. Biol. Chem., vol. 273: pp. 31788-31794, (1998).

Landry, J., et al., "The silencing protein SIR2 and its homologs are NAD-dependent protein deactylases", Proc. Natl. Aca. Sci. U.S.A., vol. 97: pp. 5807-5811 (2000).

Tanny, J.C., et al., "An enzymatic activity in the yeast Sir2 protein that is essential for gene silencing", Cell, vol. 99: pp. 735-745 (1999).

Imai, S., et al., "Transcriptional silencing and longevity protein Sir2 is an NAD-dependent histone deacetylase", Nature, vol. 403: pp. 795-800, (2000).

Smith, J.S., et al., "A phylogenetically conserved NAD+-dependent protein deacetylase activity in the Sir2 protein family", Proc. Natl. Acad. Sci. U.S.A., vol. 97: pp. 6658-6663 (2000).

Frye, R.A., "Characterization of five human cDNAs with homology to the yeast SIR2 gene: Sir2-like proteins (sirtuins) metabolize NAD and may have protein ADP-ribosyltransferase activity", Biochem. Biophys. Res. Commun., vol. 260: pp. 273-279 (1999).

Yasumasa, T., et al., "Silencing factors participate in DNA repair and recombination in *Saccharomyces cerevisiae*," Nature, 388:900-903 (1997).

Migaud, M.E., et al., "Probing aplysia californica adenosine 5'-diphosphate ribosyl cyclase for substrate binding requirements: design of potent inhibitors," Biochemistry, 38(28):9105-9114, (1999).

Oppenheimer, N.J., et al., "Stereospecificity of the intramolecular association of reduced pyridine coenzymes," Biochemistry, 17(13):2613-19, (1978).

Kumar, A., et al., "8-(4-bromo-2,3-dioxobutylthio)NAD: a new affinity label for NAD-specific isocitrate dehydrogenase," Arch. Biochem. Biophys., 308(2):357-66, (1994).

Lee, C-Y., et al., "Determination of solution structure of diphosphopyridine coenzymes with paramagnetic shift and broadening reagents," J. Magn. Reson., 17(2):151-160, (1975).

Tanny, J.C., et al., "Coupling of histone deactylation to NAD breakdown by the yeast silencing protein SIR2: evidence for acetyl transfer from substrate to a NAD breakdown product," Proc. Natl. Acad. Sci. U.S.A., 98(2):415-420, (Jan. 16, 2001).

*Primary Examiner*—Patrick T Lewis
(74) *Attorney, Agent, or Firm*—Dann, Dorfman, Herrell & Skillman, P.C.; Robert C. Netter; Kathleen D. Rigaut

(57) ABSTRACT

Novel compositions and methods are provided for identifying agents which affect chromosomal stability and aging.

7 Claims, 9 Drawing Sheets

COMPOSITIONS AND METHODS FOR IDENTIFYING AGENTS WHICH REGULATE CHROMOSOMAL STABILITY, GENE ACTIVATION AND AGING

This application is a continuation of U.S. application Ser. No. 10/416,388, filed Nov. 3, 2003 now U.S. Pat. No. 7,291,606, which is a §371 application of PCT/US01/47159, filed Nov. 13, 2001, which claims priority to U.S. Provisional Application No. 60/247,827, filed Nov. 10, 2000. Each of the foregoing Application is incorporated herein by reference in its entirety.

Pursuant to 35 U.S.C. §202(c) it is acknowledged that the U.S. Government has certain rights in the invention described herein, which was made in part with funds from the National Institutes of Health, Grant Number: GM59785.

FIELD OF THE INVENTION

Several publications are referenced in this application by numbers in parentheses in order to more fully describe the state of the art to which this invention pertains. The disclosure of each of these publications is incorporated by reference herein.

The SIR2 (silent information regulator 2) gene family of proteins is conserved from bacteria to man (1). In yeast, SIR2 is required for transcriptional silencing (2), and is also involved in suppressing rDNA recombination and controlling life span (3, 4). Very little is known about the roles of four other SIR2 family members found in yeast (5), nor about the function of homologs from other species. The Salmonella typhimurium homolog, CobB, can substitute for CobT as a phosphoribosyl transferase during cobalamin biosynthesis (6). In-vitro, CobB has histone/protein deacetylase activity (7, 8). Given the widespread occurrence and extensive conservation of the SIR2-like proteins, understanding their molecular mechanism is essential for identifying the cellular roles played by these proteins. Unfortunately, discrepancies among recent reports (7-11) have added to the general uncertainty as to the true enzymatic function for this family of proteins. These reports have suggested that the SIR2 proteins are either histone ADP-ribosyltransferases (9, 11), or histone/protein deacetylases (7, 8), or both (10).

SUMMARY OF THE INVENTION

In accordance with the present invention, a novel acetyl-ADP ribose compound (O-acetyl-ADP ribose) has been identified as the primary product of the histone deacetylase reaction catalyzed by the HTS2 protein. The availability of O-acetyl-ADP ribose facilitates production of immunologically specific antibodies for isolating this molecule. Such antibodies may be polyclonal or monoclonal. Antibodies immunologically specific for O-acetyl ADP ribose may be used to advantage in competitive binding assays to identify test compounds having affinity for O-acetyl ADP ribose. Test compounds so identified are also within the scope of the present invention.

Methods for producing the novel O-acetyl ADP ribose of the invention as well as analogs thereof are also provided.

In yet a further aspect, pharmaceutical compositions containing the novel compounds of the invention are provided. Such pharmaceutical compositions should have efficacy as anti-aging and anti-cancer agents.

BRIEF DESCRIPTION OF THE DRAWINGS

FIG. 5C: Single turnover rapid quench-flow analysis. HST2 (10 mM) and NAD$^+$ (300 mM) were rapidly mixed with 2.5 mM [$^3$H]-AcLys14 H3 peptide at 22±3° C., pH 7.5 in a Hi-Tech Rapid Quench-Flow Device RQF-63. Between 31 msec-8 sec, reactions were quenched with TFA (1%). Quantification of [$^3$H]-AcLys14 H3 peptide (diamonds) and the [$^3$H]-acetate-adduct (circles) was accomplished by liquid scintillation counting of these species separated using reverse phase HPLC. Data were fitted to a single exponential, yielding rate constants of 2.0±0.1 s$^{-1}$ for [$^3$H]-AcLys14 H3 peptide deacetylation and 2.3±0.2 s$^{-1}$ for [$^3$H]-acetate-adduct formation.

FIG. 6A). For comparison, authentic ADP ribose yielded a predicted mass of 560 (FIG. 6B). With both ADP ribose and acetyl-ADP ribose, masses corresponding to the association of 1 and 2 sodium ions were also observed.

FIG. 7 shows a proposed catalytic mechanism for the production of O-acetyl-ADP ribose. Acetyl-lysine condenses directly with the oxo-carbenium cation, which resulted from the elimination of nicotinamide from $NAD^+$. A hydroxide ion then attacks this intermediate to form a tetravalent intermediate, which can collapse to produce 1-O-acetyl-ADP ribose (Compound I, FIG. 7). The 1-O-acetyl-ADP ribose may then be attacked by the adjacent 2' OH group (via enzyme-assisted general base catalysis) to produce the 2-O-acetyl-ADP ribose (Compound II, FIG. 7). Once in bulk solution, the 2-O-acetyl-ADP ribose appears to be in rapid equilibrium with its solution migration adduct 3-O-acetyl-ADP ribose (Compound III, FIG. 7). Additional quantitative HPLC analysis followed by 2-dimentional NMR (heteronuclear multiple bond correlation) experiments have revealed the migration and equilibrium among the O-acetyl ADP ribose adducts depicted in FIG. 7. The enzymatic reaction could occur in either stepwise or concerted fashion. For clarity, we have drawn the chemical events as stepwise events.

FIG. 9A, HPLC (reversed phase) elution trace of O-acetyl-ADP-ribose enzymatically produced by the NAD-dependent deacetylase HST2. The product was purified using two sequential reversed phase separations. Vertical marks are strip-chart ticks of the fraction collector. The peak was collected and lyophilized; the product was then resuspended in TFA/acetonitrile/water and re-lyophilized to complete dryness until use. Purified O-acetyl-ADP-ribose was solubilized in PBS and microinjected into immature starfish oocytes at final 1 mg/mL. Maturation hormone (1-methyladenine) was then added, and images were taken at 3 (FIG. 9B) and 24 hr (FIG. 9C) post hormone treatment. Control oocytes were injected with PBS. By 3 hr, normal/control oocytes display GV breakdown, and by 24 hr (if not fertilized) will undergo programmed cell death (apoptosis) (see controls). The O-acetyl-ADP-ribose injected oocytes did not undergo GV breakdown or polar body extrusion, nor did they undergo apoptosis. Instead, they remained in a state of stasis.

(FIG. 10A) The egg on the right was injected with 200 nM final HST2, the oocytes were then matured by addition of 10 µM 1-MA, and fertilized 4 hours later. The control egg matured, and fertilized while the injected egg failed to mature, and therefore was incompetent for fertilization. 10 of 10 eggs injected in this chamber behaved the same way. (FIG. 10B) The egg on the right is injected with R45AHST. The oocytes were matured by addition of 10 µM 1-MA, and fertilized four hours later. Both eggs matured and were fertilized normally 4 hours later. 7 of 7 injected eggs in the same chamber behaved the same way. (FIG. 10C) One blastomere of the 2 cell stage embryo on the left was injected with 200 nM HST2 WT. The injection was done after complete cytokinesis. The injected blastomere divided once, then both daughters stopped, while the sister which saw no dose, went on to form a Formal blastula.

DETAILED DESCRIPTION OF THE INVENTION

Conflicting reports have suggested that the SIR2 (silent information regulator 2) protein family employs $NAD^+$ to either ADP-ribosylate histones (1, 9), or deacetylate histones (7, 8) or both (10). Uncovering the true enzymatic function of SIR2 is critical to the basic understanding of its cellular function. Therefore, we set out to authenticate the reaction products and to determine the intrinsic catalytic mechanism. We provide direct evidence that the efficient histone/protein deacetylase reaction is tightly coupled to the formation of a novel acetyl-ADP ribose product (O-acetyl-ADP ribose). One molecule of $NAD^+$ and acetyl-lysine are readily catalyzed to one molecule of deacetylated lysine, nicotinamide, and O-acetyl-ADP ribose. A unique reaction mechanism involving the attack of enzyme-bound acetate or direct attack of acetyl-lysine on an oxo-carbenium ADP ribose intermediate is proposed. It appears that the previously reported histone/protein ADP-ribosyltransferase activity is a low efficiency side reaction that can be explained through the partial uncoupling of the intrinsic deacetylation and acetate transfer to ADP ribose.

Also provided herein is data revealing that O-acetyl-ADP ribose plays a pivotal role in cell cycle control. This observation provides support for the utilization of O-acetyl-ADP ribose and its analogs as anti-cancer agents and anti-aging compounds.

I. Antibodies Immunologically Specific for O-Acetyl-ribose

The present invention also provides antibodies capable of immunospecifically binding to O-acetyl-ADP ribose. Polyclonal antibodies directed toward O-acetyl-ADP ribose may be prepared according to standard methods. In a preferred embodiment, monoclonal antibodies are prepared, which react immunospecifically with various epitopes of O-acetyl-ADP ribose. Monoclonal antibodies may be prepared according to general methods of Köhler and Milstein, following standard protocols. Polyclonal or monoclonal antibodies that immunospecifically interact with O-acetyl-ribose can be utilized for identifying and purifying the compound. For example, antibodies may be utilized for affinity separation of proteins with which they immunospecifically interact. Antibodies may also be used to identify cells containing O-acetyl-ADP ribose. O-acetyl-ribose-specific antibodies may also be used to immunoprecipitate proteins which bind O-acetyl-ribose from a sample containing a mixture of proteins and other biological molecules. Other uses of anti-O-acetyl-ribose antibodies are described below.

Antibodies according to the present invention may be modified in a number of ways. Indeed the term "antibody" should be construed as covering any binding substance having a binding domain with the required specificity. Thus, the invention covers antibody fragments, derivatives, functional equivalents and homologues of antibodies, including synthetic molecules and molecules whose shape mimics that of an antibody enabling it to bind an antigen or epitope.

Exemplary antibody fragments, capable of binding an antigen or other binding partner, are Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab') 2 fragments, a bivalent fragment including two Fab fragments linked by a disulphide bridge at the hinge region. Single chain Fv fragments are also included.

Humanized antibodies in which CDRs from a non-human source are grafted onto human framework regions, typically with alteration of some of the framework amino acid residues, to provide antibodies which are less immunogenic than the parent non-human antibodies, are also included within the present invention.

I. Rational Drug Design

According to one aspect of the invention, methods of screening agents to identify suitable drugs for inhibiting or augmenting the histone/protein deacetylase reaction are provided herein.

O-acetyl-ADP ribose employed in protein binding assays may either be free in solution, affixed to a solid support or within a cell. One method of screening for compounds which bind 1-O-acetyl-ribose utilizes eukaryotic or prokaryotic host cells which are stably transformed with recombinant polynucleotides expressing the HST2 or SIR2 gene polypeptide or fragment, preferably in competitive binding assays. Such cells, either in viable or fixed form, can be used for standard binding assays. One may determine, for example, formation of complexes between a O-acetyl-ribose and a protein present in the cell. Alternatively, such cells may be contacted with test compounds to identify novel test compounds which bind either the deacetylase enzyme or the O-acetyl ribose reaction product. Such assays provide the means to assess the degree to which the formation of a complex between the deacetylase enzyme or O-acetyl-ribose and a known ligand is interfered with by the agent being tested.

Another technique for drug screening provides high throughput screening for compounds having suitable binding affinity to O-acetyl-ribose and is described in detail in Geysen, PCT published application WO 84/03564, published on Sep. 13, 1984. Briefly stated, large numbers of different, small peptide test compounds are synthesized on a solid substrate, such as plastic pins or some other surface. The peptide test compounds are reacted with O-acetyl-ribose and washed. Bound O-acetyl-ribose is then detected by methods well known in the art.

Purified O-acetyl-ribose can also be coated directly onto plates for use in the aforementioned screening techniques.

This invention also contemplates the use of competitive drug screening assays in which neutralizing antibodies capable of specifically binding the O-acetyl-ribose compete with a test compound for binding to the O-acetyl-ribose. In this manner, the antibodies can be used to detect the presence of molecules which share one or more antigenic determinants of the O-acetyl-ribose compound.

The goal of rational drug design is to produce structural analogs of biologically active polypeptides of interest or of small molecules with which they interact (e.g., agonists, antagonists, inhibitors) in order to fashion drugs which are, for example, more active or stable forms of the compound of the invention, or which, e.g., enhance or interfere with the function of a O-acetyl ribose in vivo. See, e.g., Hodgson, (1991) Bio/Technology 9:19-21. In one approach, one first determines the three-dimensional structure of a small molecule of interest (e.g., O-acetyl-ribose) or, for example, of the O-acetyl-ribose-deacetylase complex, by x-ray crystallography, by nuclear magnetic resonance, by computer modeling or most typically, by a combination of approaches. Less often, useful information regarding the structure of a compound may be gained by modeling based on the structure of similar compounds. An example of rational drug design is the development of HIV protease inhibitors.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate small molecules from banks of chemically or biologically produced banks of molecules. Selected molecules would then act as the pharmacore.

Thus, one may design drugs which have, e.g., improved O-acetyl-ribose activity or stability or which act as inhibitors, agonists, antagonists, etc. of the reaction in which O-acetyl-ribose is formed. By virtue of the availability of isolated O-acetyl-ribose, sufficient amounts of the compound may be made available to perform such analytical studies as x-ray crystallography. In addition, the knowledge of the O-acetyl-ribose structure provided herein will guide those employing computer modeling techniques in place of, or in addition to x-ray crystallography.

III Therapeutics

Agents identified by the above described methods of the invention can be formulated in pharmaceutical compositions for the treatment of cancer and aging. Changes in histone acetylation levels play a central role in the regulation of neoplasia, tumor suppression, cell cycle control, hormone response, chromosome stability and senescence. Reversible histone acetylation controls gene transcription. The proper level of histone acetylation is regulated by histone acetyltransferase activity and by histone deacetylase activity. Recent results on gene specific effects have provided a rationale basis for the development of histone deacetylase inhibitors as antitumor agents. Furthermore, many tumor suppressor genes are known to be inactivated by promoter DNA hypermethylation, a process which is closely linked to histone deacetylation and chromatin structure. DNA methylation and histone deacetylation act synergistically in silencing genes involved in cancer. Also, many acute leukemias are caused by fusion proteins that have been created by chromosomal translocations involving histone acetyltransferases.

The SIR2 NAD-dependent histone deacetylase also appears to play a role in aging (18). Recently, the observation that caloric restriction leading to increased life-span appears to be linked through an $NAD^+$ and SIR2-dependent pathway (18), raising the possibility that O-acetyl-ADP ribose or its direct metabolites may play a role in this phenomenon. This finding indicates that O-acetyl-ADP ribose or its analogs may affect the anti-aging process when taken as a therapeutic or as a dietary supplement.

These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual.

The following materials and methods are provided to facilitate the practice of the present invention.

Materials. [$^3$H]Acetyl-CoA (1.88 Ci/mmol) and Na-[$^3$H]-acetate (100,000 cpm/nmol) was from NEN Life Sciences Products. Nicotinamide, ADP-ribose, and nicotinamide adenine dinucleotide (NAD) were purchased from Sigma Chemical Company. Histone H3 peptide, ARTKQTARKSTGGKAPP-KQLC and the Lysine 14 acetylated H3 peptide (AcLys-14), corresponding to the 20 amino-terminal residues of human histone H3 was synthesized by the Protein Chemistry Core Lab at Baylor College of Medicine. Histidine tagged full length HST2 was recombinantly expressed and purified from Escherichia coli BL21DE3 bacteria using a T7 polymerase-based expression. Harvested cells were lysed by French pressure in 50 mM Tris, pH 8.0, 300 mM NaCl, 1 mM β-mercaptoethanol with protease inhibitors (0.1 mM phenylmethylsulfonyl fluoride, 10 μg/mL leupeptin, and 5 μg/mL aprotinin). The clarified extract was rocked batchwise with Ni-NTA-agarose (Qiagen) (2 mL) for 1 h at 4° C. The Ni-NTA-agarose was then applied to a small column and washed with 50 mM Tris, pH 8.0, 300 mM NaCl, 1 mM 2-mercaptoethanol. HST2 protein was eluted with a linear 0-500 mM imidazole gradient. HST2 eluted at 200 mM imidazole and was determined to be >95% pure by scanning densitometry of commassie-stained SDS-PAGE. Imidazole was remove by extensive dialysis in the above mentioned Tris buffer. CobB and SIR2 proteins were purified as described (7).

Catalytic Analysis by HPLC. Standards of AcLys-14 H3 peptide and NAD$^+$ (HST2 substrates), and potential products of the HST2 reaction, H3 peptide, nicotinamide, [$^3$H]-acetate and ADP-ribose were resolved by reverse phase HPLC on a Beckman Ultrasphere column (4.6 mm by 15 cm). Samples were injected in 0.05% TFA/H$_2$O for 1 min prior to a linear gradient of 0-40% acetonitrile in 1-41 min. The peaks of absorbance at 214/260 nm were collected and subjected to mass spectral analysis. [$^3$H]-acetate was detected by liquid scintillation counting. To authenticate the reaction products, HST2 (3.6 μM) was mixed with substrates AcLys-14 H3 peptide (525 μM) and NAD$^+$ (175 μM) and allowed to react at 37° C. for 5 min prior to quenching with TFA to 1%. Substrates and products were resolved on reverse phase HPLC and subjected to mass spectral analysis.

Typical HST2 steady-state reactions to monitor deacetylation of AcLys-14 H3 peptide or nicotinamide formation were carried out at 37° C. in 50 mM Tris, pH 7.5 buffer. Rates of product formation were determined at various concentrations of AcLys-14 H3 peptide (5-300 μM) and NAD$^+$ (5-600 μM). During the linear portion of the initial velocity, the reactions were quenched with TFA to 1% and product formation was monitored by the HPLC analysis described above. Standard curves were generated to quantify H3 peptide and nicotinamide product formation by injecting known amounts of authentic standards and monitoring the corresponding peak height at 214 nm. The standard curves were linear in the range of 0-2 nmol and were reproducible from day to day.

P/CAF [$^3$H]-monoacetylation of H3 peptide. The histone acetyltransferase P/CAF was used to monoacetylate H3 peptide on Lysine 14 (12). P/CAF (0.175 μM) was mixed with [$^3$H]-acetyl CoA (33.3 μM, 1.88 Ci/mmol) and H3 peptide (175 μM) for 20 min at 25° C. prior to quenching with TFA to 1%. Mono [$^3$H]-acetylated H3 peptide was separated from unmodified H3 by HPLC analysis as described above.

MALDI/ESI Mass Spectrometry Analyses. MALDI mass spectrometry was performed (Oregon State University, Environmental Health Sciences Center) on a custom-built reflector time-of-flight mass spectrometer equipped with a two-stage delayed extraction source. Approximately 1 μL of sample solution was mixed with 2 μL 2,4,6-THAP (2,4,6-trihydroxy acetophenone; 10 mg/ml in 70:30 water/acetonitrile, plus 50 mg/mL diammonium citrate in water); a 1.0 μL droplet of this analyte/matrix solution was deposited onto a matrix precrystallised sample probe and allowed to dry in air. Mass spectra were produced by irradiating the sample with a (355 nm) Nd:YAG laser (Spectra Physics) and operating the ion source at 23 kV with a 150 ns/1.0 kV delay. Every mass spectrum was recorded as the sum of 20 consecutive spectra, each produced by a single pulse of photons. Ions from an added standard were used for mass calibration. ESI mass spectrometry was also carried out at Emory University School of Medicine Microchemical Facility. Precursor ion (phosphate anion) scanning procedure was performed as described (13). Chemical data base searches (Available Chemical Directory Data Base, MDL Information Incorporated; cas-online, American Chemical Society; SciFinder Scholar, American Chemical Society) revealed that O-acetyl ADP ribose is a novel compound.

Rapid-Reaction Kinetic Analysis. For the quench-flow analysis under single turnover conditions, HST2 (10 μM) and NAD$^+$ (300 μM), were rapidly mixed with 2.5 μM [$^3$H]-AcLys14 H3 peptide at 22±3° C., pH 7.5 in a Hi-Tech Rapid Quench-Flow Device RQF-63. After various reactions times between 31 msec-8 sec, the reactions were quenched with TFA to a final concentration of 1%. The amount of [$^3$H]-AcLys14 H3 peptide and [$^3$H]-O-acetyl ADP ribose was determined by liquid scintillation counting of these species separated on reverse phase HPLC.

Methods for monitoring O-acetyl-ADP ribose utilization by enzymes from human HeLa cell extracts. HeLa Cells were grown at 37° C. in Dulbecco's Modified Eagles Medium containing D-glucose 1 g/L, L-glutamine 1 g/L, pyridoxine hydrochloride 1 g/L, sodium pyruvate 110 mg/L, 10% fetal bovine serum (FBS), penicillin at 1000 units/mL, and streptomycin at 1 mg/mL (Gibco BRL) (growth medium). When cells had reached 80-90% confluency, they were rinsed once with PBS, lysed in 100-200 μL of ice-cold, 20 mM Tris, pH 7.2, 137 mM NaCl, 10% glycerol, 1% Nonidet P-40, 100 μM phenylmethylsulfonyl fluoride (PMSF), 20 μg/mL leupeptin, and 20 μg/mL of aprotinin. Cells were scraped into eppendorf tubes, sonicated for 10 s, and centrifuged at 16,000×g for 10 min to remove cell debris. Protein concentrations of supernatants were determined by the method of Bradford. Lysates (40 μL) of the cells or buffer controls were then incubated with radiolabeled 1-O-acetyl-ADP ribose (about 0.5 nmol) (total volume of reaction was 100 μL) for the indicated times prior to analysis by reverse phase HPLC. The HPLC analysis was carried out as described previously.

Collection of Gametes and Microinjection

Asterina miniata gametes were collected and microinjections were performed as described previously (Carroll et al., 1999). Briefly, quantitative microinjection of Asterina miniata oocytes was performed at 16° C., using mercury-filled micropipets (Hiramoto, 1962; Kiehart, 1982; and see the information available at http://egg/uchc.edu/injection), allowing injection of precisely calibrated picoliter volumes into the oocytes and blastomeres. Injection volumes were 3% of the total cellular volume (for oocytes, 93 pL and for blastomeres, 47 pL). Buffer alone, purified O-acetylated ADP ribose or recombinant protein was injected into immature oocytes or one blastomere of a two cell stage embryo to a final concentration in the cytoplasm as indicated in the figure legends and Tables. 1-methyl adenine was from Sigma and was used at 10 µM.

Preparation of Oocyte Extracts

Oocyte suspensions were centrifuged (280×g) briefly and the seawater was removed. Oocytes were resuspended in lysis buffer (PBS, pH 7.4, 15 mM disodium-EGTA, 1% Triton x-100, 0.5 mM sodium vanadate, 1 mM sodium fluoride, 10 µM each of aprotonin, leupeptin, and benzamadine, 50 µM PMSF) and lysed by passage through a 27.5 gauge needle on ice. The sample was centrifuged at 18,000×g at 4° C. for 20 min and the soluble fraction was collected and kept on ice. Protein concentration was determined using the Pierce BCA assay using BSA as a standard. Aliquots were snap frozen in liquid nitrogen and stored at −80° C.

The following examples are provided to illustrate various embodiments of the invention. They are not intended to limit the invention in any way.

EXAMPLE I

Figure 1:
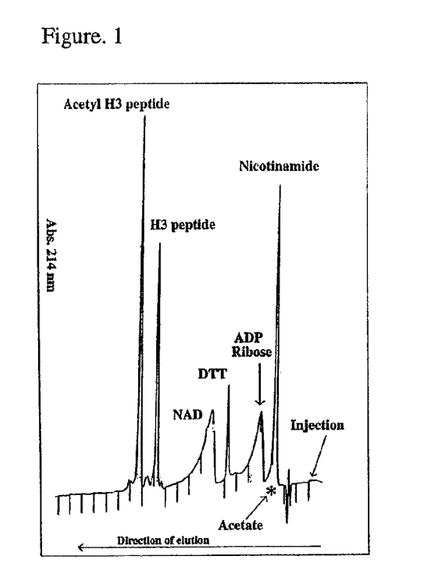
FIG. 1 shows reverse phase HPLC elution of substrate standards (NAD$^+$ and AcLys-14 H3 peptide) and of potential products (H3 peptide, acetate, ADP ribose, and nicotinamide). Approximately 1.5 nmol of AcLys-14 H3 peptide, 1.0 nmol of H3 peptide, 10 nmol NAD, 15 nmol ADP ribose, and 15 nmol of nicotinamide were mixed and subjected to reverse phase chromatography. In a separate HPLC run, 1.0 nmol of Na—[$^3$H]-acetate (100,000 cpm/nmol) was subjected to chromatography. Order of elution: nicotinamide, acetate, ADP-ribose, NAD$^+$, H3 peptide and AcLys-14 H3 peptide. The elution position of acetate (denoted with an asterisk) was determined using authentic [$^3$H]-acetate and detection by liquid scintillation counting. All others were detected by UV absorption at 214 nm.

Due to the high yield and activity of recombinant enzyme, the yeast SIR2 homolog HST2 was utilized as the prototypical SIR2 member for the extensive study described here. Where noted, yeast SIR2 and the *Escherichia coli* homolog, CobB, were employed to demonstrate the conservation in catalytic function among the family. Although the requirement for NAD$^+$ has been demonstrated, surprisingly, the true identity and stoichiometry of the products has not been investigated. The extent of coupling between NAD$^+$ consumption and histone deacetylation was examined initially using the monoacetylated histone H3 peptide ARTKQTARKSTGG (AcK)APRKQL (corresponding to the first 20 amino-terminal residues in histone H3), subsequently referred to as AcLys-14 H3 peptide. To unambiguously identify the authentic products of the NAD-dependent deacetylation reaction, HST2 catalyzed products were resolved and quantified by reverse phase HPLC, and verified by mass spectrometry. First, standards of substrates (NAD$^+$ and AcLys-14 H3 peptide) and of the potential products (H3 peptide, acetate, ADP ribose, and nicotinamide) were separated on reverse phase HPLC (FIG. 1). The components eluted in the order: nicotinamide, acetate, ADP-ribose, NAD$^+$, H3 peptide and AcLys-14 H3 peptide. The elution position of acetate was determined using [$^3$H]-acetate and detection by liquid scintillation counting, whereas all others were detected by UV absorption at 214 nm or 260 nm (FIG. 1).

Figure 2:
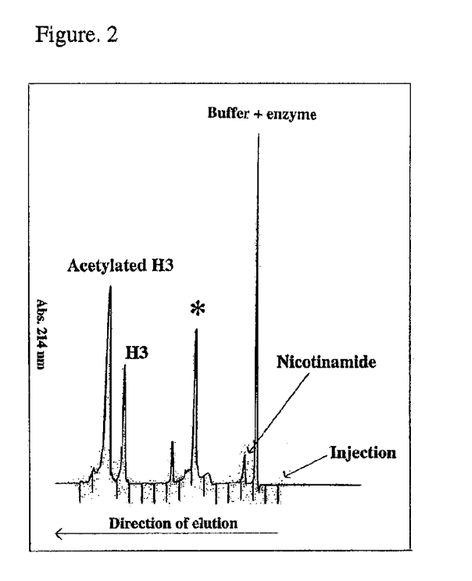
FIG. 2 shows elution of products from the HST2 NAD-dependent deacetylation reaction, detected by UV absorbance at 214 nm. Novel product is denoted with an asterisk. Conditions: 3.6 µM HST2, 175 µM NAD$^+$, 525 µM Lys14 AcH3, 1 mM DTT, 37° C. for 30 minutes prior to quenching with TFA to final concentration of 1%.
Figure 3:
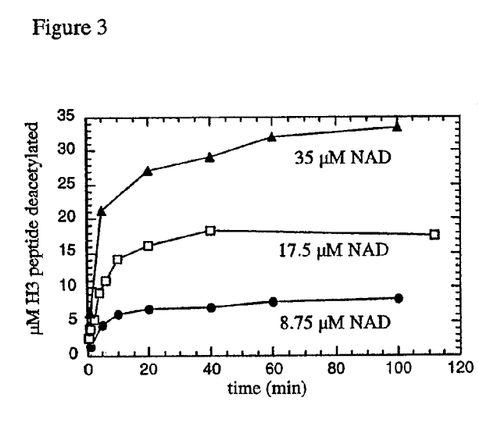
FIG. 3 is a graph showing that the amount of deacetylation correlates exactly with the consumption of NAD$^+$. This graph displays the progress curves of deacetylation at fixed, but limiting [NAD$^+$]. HST2 reaction was allowed to proceed to completion under various limiting [NAD$^+$] and the amount of deacetylated H3 peptide was determined. Conditions: 375 nM HST2, 175 µM Lys14 AcH3, 8.75, 17.5, or 35 µM NAD$^+$, 1 mM DTT, 37° C. for 20 min prior to quenching with TFA to 1%.
Figure 4:
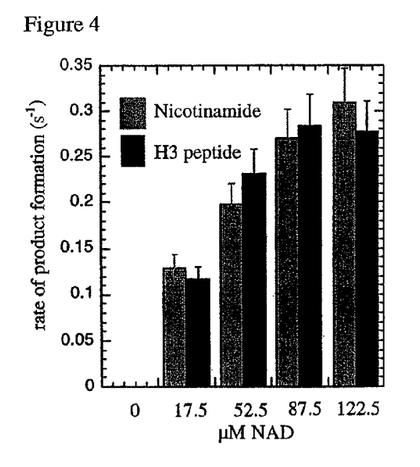
FIG. 4 is a graph showing steady-state rate of nicotinamide and deacetylated H3 peptide formation at various fixed [NAD$^+$]. Conditions: 375 nM HST2, 175 µM Lys14 AcH3, 8.75 µM to 280 µM NAD$^+$, 1 mM DTT, 37° C. for 1 min prior to quenching with TFA to a final concentration of 1%.

HST2 deacetylation reactions in the absence of NAD$^+$ produced no detectable H3 peptide deacetylation or nicotinamide formation, consistent with the previously described NAD-dependence (7, 8, 10). When NAD$^+$ was included, robust deacetylation and nicotinamide formation was observed (FIG. 2). However, to our great surprise no significant amounts of ADP ribose were detected (FIG. 2). Nicotinamide and ADP ribose are the predicted products from the hydrolysis of the NAD$^+$ glycosidic bond. To explore this finding and establish the degree of coupling between NAD$^+$ consumption and AcLys-14 H3 peptide deacetylation, the amount of deacetylated H3 formed and the amount of NAD$^+$ consumed were determined (FIG. 3). Moles of product formed in the enzyme-catalyzed reaction were calculated from standard curves generated with known amounts of authentic H3 peptide and nicotinamide. In reactions using several different initial concentrations of NAD$^+$, every mole of NAD$^+$ consumed by the enzyme produced one mole of deacetylated H3 peptide, suggesting that these two chemical events are tightly coupled. Mass spectrometry confirmed the identity of nicotinamide and deacetylated H3 peptide as the HPLC product peaks co-eluting with authentic standards (FIGS. 1 and 2). The previously described NAD$^+$:nicotinamide exchange reaction was consistent with nicotinamide being a product of the reaction (7). The tight coupling of nicotinamide formation and H3 deacetylation was established further by comparing the steady-state rate of nicotinamide formation with the rate of AcLys-14 H3 peptide deacetylation (FIG. 4). The NAD-concentration dependence of the steady-state rate of AcLys-14 H3 deacetylation matches exactly the rate of nicotinamide formation (FIG. 4). Substrate saturation curves indicated that the $K_m$ for NAD$^+$ is 70 µM and the $K_m$ for AcLys-14 H3 is estimated to be less than 500 nM. The fact that NAD$^+$ is consumed in the reaction indicates that it is not an allosteric regulator, but rather a bona fide substrate. Together, these results (FIGS. 2 and 3) suggested an exquisitely-linked enzymatic reaction in which NAD$^+$ cleavage and deacetylation are directly coupled.

Figure 5A:
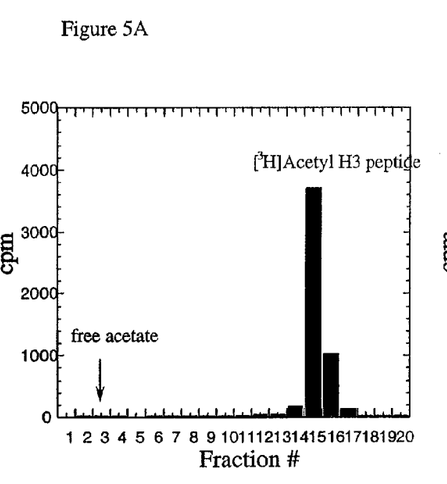
FIGS. 5A-5C are a series of graphs showing that acetate is not a primary product of HST2-catalyzed histone/protein deacetylation. H3 peptide was stoichiometrically acetylated on Lys-14 by the histone acetyltransferase P/CAF and using [$^3$H]-AcCoA. Monoacetylated [$^3$H]-AcLys-14 H3 peptide was then purified by HPLC (FIG. 5A) and utilized as a substrate in the HST2 deacetylation reactions (FIG. 5B). Upon complete consumption of [$^3$H]-AcLys-14 H3 by HST2, all of the original [$^3$H] from H3 peptide was converted to a labeled product that eluted much later than authentic acetate. Conditions: 375 nM HST2, 175 µM NAD$^+$, 5 µM [$^3$H]-Lys14 AcH3, 1 mM DTT, for 1 min at 37° C. prior to quenching with TFA to a final concentration of 1%.
Figure 5B:
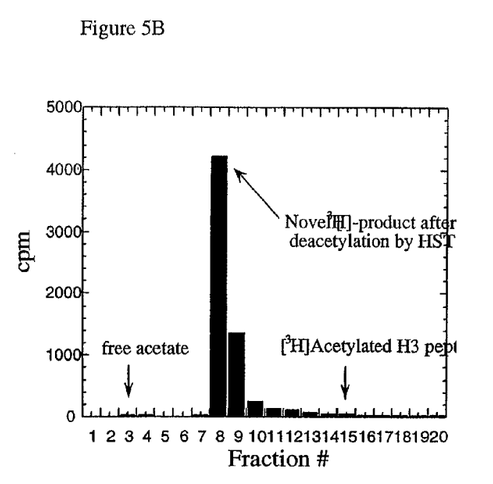

Next, we attempted to verify and quantify acetate as one of the obligate products. To accomplish this, H3 peptide was stoichiometrically acetylated on Lys-14 by the histone acetyl-transferase P/CAF using [$^3$H]-AcCoA. Monoacetylated [$^3$H]-AcLys-14 H3 peptide was then purified by HPLC (FIG. 5A) and utilized as a substrate in the HST2 deacetylation reaction (FIG. 5B). To our surprise, the product profiles clearly indicated that acetate was not the primary product in the reaction. The HPLC elution position of the radioactive [$^3$H]-acetate product (FIG. 5B) did not correspond to the position of authentic acetate (FIG. 1). Instead, the [$^3$H]-labeled product eluted at a position that was significantly more hydrophobic than ADP-ribose. Upon complete consumption of the [$^3$H]-AcLys-14 H3 peptide, only a trace amount of acetate (<2% of total product formed) was detected in the reactions, whereas >98% of the original radioactivity from [$^3$H]-AcLys-14 H3 was transferred to a novel acetate adduct (FIG. 5B). Control experiments in the absence of enzyme did not result in transfer of acetate to this more hydrophobic form. Also, the acetate-adduct was not formed from a non-enzymatic solution reaction between the putative products [$^3$H]-acetate, ADP ribose, nicotinamide, and H3 peptide.

Figure 5C:
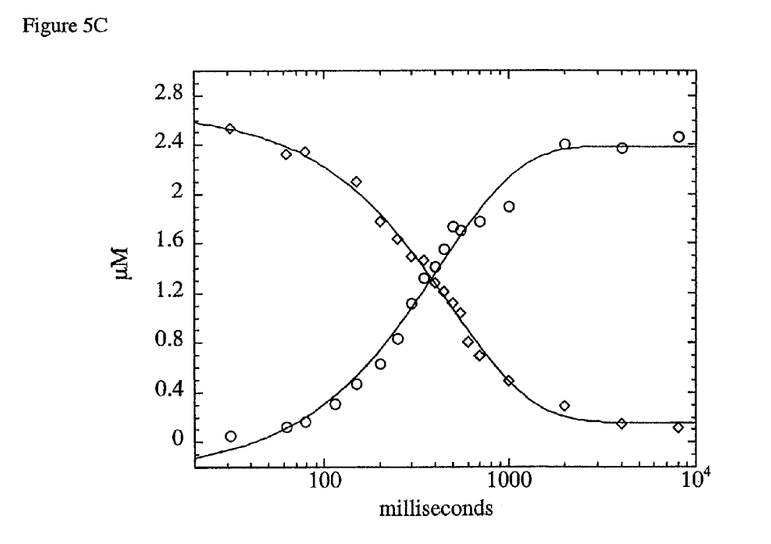

To explore the idea that the acetate-adduct was a direct product of enzymatic deacetylation and not the product of a slower side-reaction, a rapid-reaction single turnover experiment was performed. Using a quench-flow apparatus, HST2 was rapidly reacted with excess NAD$^+$ and sub-stoichiometric levels of [$^3$H]-AcLys-14 H3. Under these conditions, the enzyme will perform only a single round of catalysis, allowing us to quantify the time-dependent loss of [$^3$H]-AcLys-14 H3 and the generation of the [$^3$H]-acetate-adduct. At various times between 30 ms and 8 s, the reactions were quenched and were analyzed by HPLC and liquid scintillation counting. The progress curves (FIG. 5C) for the rapid single turnover clearly demonstrated that AcLys-14 H3 substrate consumption (rate constant of 2.0±0.1 s$^{-1}$) and acetate-adduct formation (rate constant of 2.3±0.2 s$^{-1}$) were concomitantly linked, providing strong evidence that the acetate-adduct is a primary product of HST2-catalyzed deacetylation.

UV/VIS spectral analysis revealed that the acetate-adduct absorbed strongly at 260 nm, consistent with an analog containing an adenine ring. During catalytic turnover, the appearance of a new UV-absorbing species (FIG. 2) correlated exactly with the fractions containing the [$^3$H]-labeled product (FIG. 5B). Since ADP ribose was not detected as a bona fide product of the reaction (FIG. 2), it was logical to suggest that the novel product was an adduct between ADP ribose and acetate. In similar experiments with SIR2 and CobB, the identical-eluting radioactive product was observed and, again, no acetate or ADP ribose were detected as primary products in these reactions.

Figure 6A:
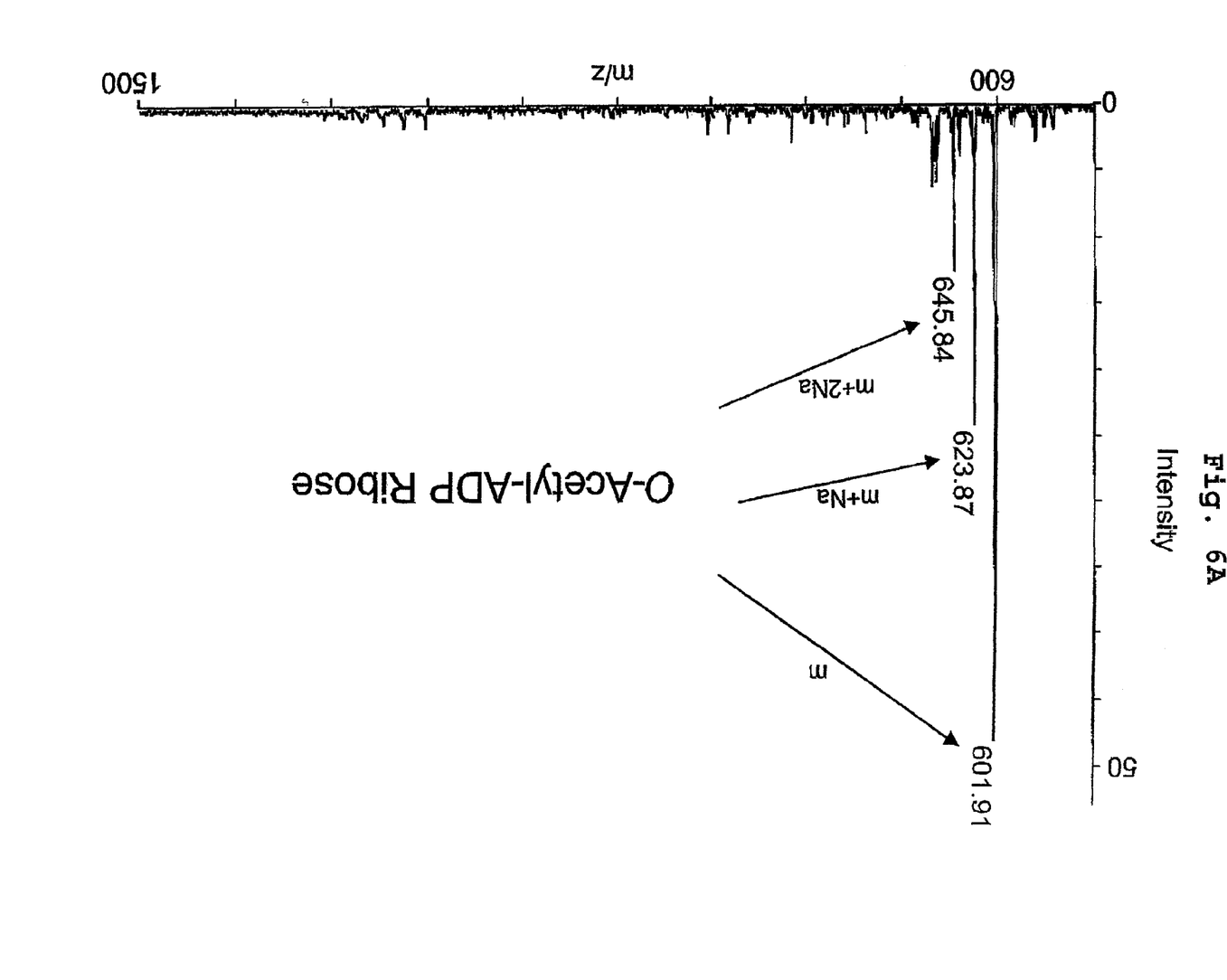
FIGS. 6A and 6B show mass spectral analysis of the novel product generated by HST2-catalyzed histone/protein deacetylation. MALDI mass spectrometry was used to identify a mass of 602, consistent with the formation of acetyl- ADP ribose (O-acetyl-ADP ribose.
Figure 6B:
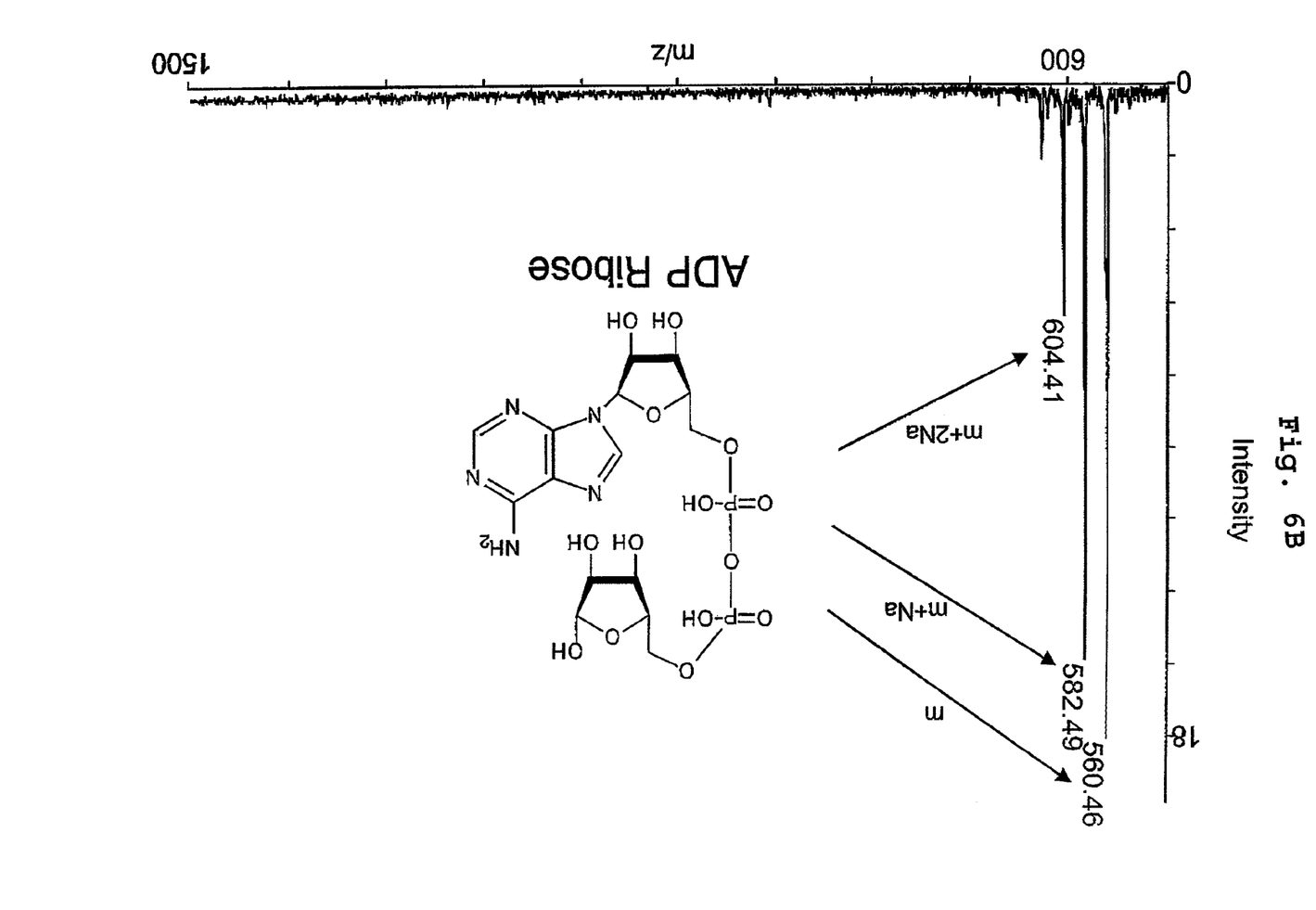
Figure 7:
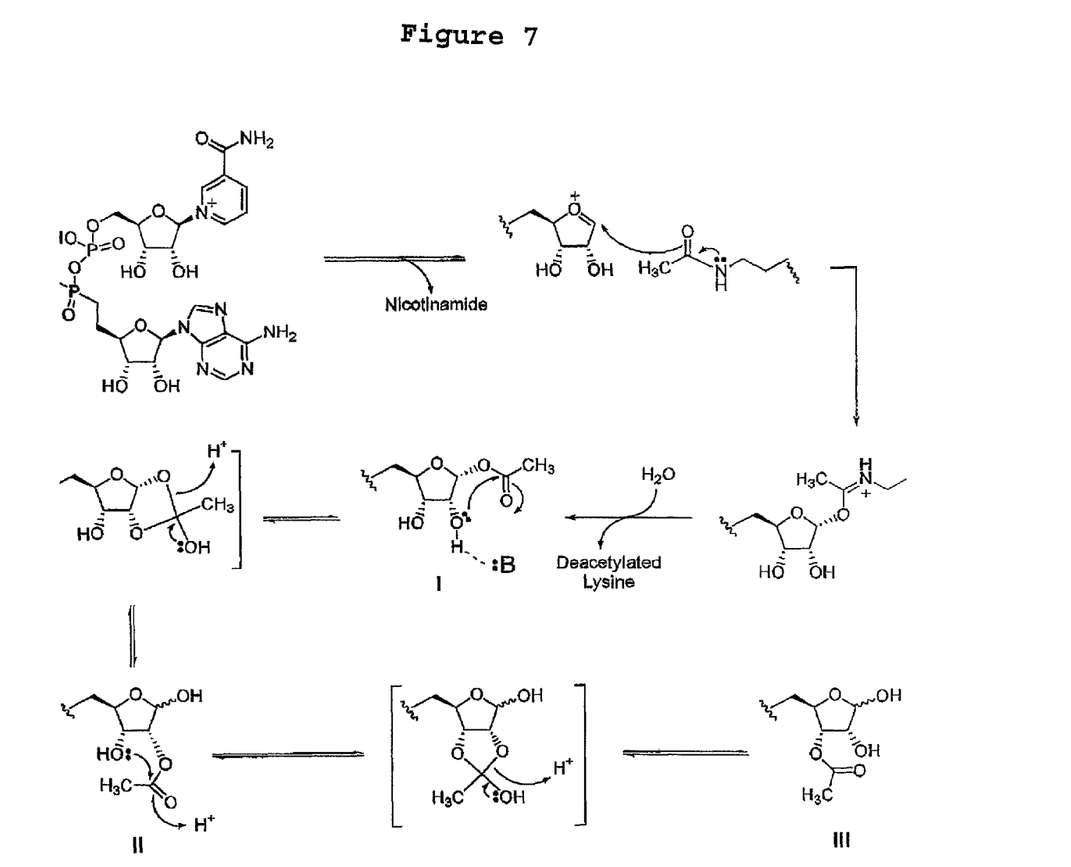

To confirm our hypothesis that an adduct between ADP ribose and acetate is the authentic product, HPLC fractions containing this product were subjected to both MALDI and ESI mass spectral analysis for mass determination. The novel adduct yielded a mass (positive molecular ion in MALDI) of 602 (FIG. 6A), consistent with the enzymatic formation of acetyl-ADP ribose. For comparison, the mass results of an ADP-ribose standard are displayed in FIG. 6B, indicating the predicted mass of 560. The difference of 42 between the two masses is equivalent to the difference between replacing a hydrogen on an ADP-ribose hydroxyl with an acetyl group. Confirming these results, the identical mass was also observed by separate ESI/MALDI analyses from samples submitted to two independent facilities. Consistent with the formation of an O-acetyl bond to ribose, hydroxylamine treatment of the acetyl-ADP ribose compound liberated free ADP ribose. Similarly, high glycine concentrations also liberated ADP ribose from the HST2, SIR2, and CobB-catalyzed formation of acetyl-ADP ribose. Thus, we provide direct evidence that the efficient histone/protein deacetylase reaction is tightly coupled to the formation of a novel acetyl-ADP ribose product. One molecule of $NAD^+$ and acetyl-lysine (histone) are readily catalyzed to one molecule of deacetylated lysine, nicotinamide and acetyl-ADP ribose. Although mass spectrometry cannot provide direct information on the position of the acetyl group on ADP ribose, the chemical evidence discussed below suggests that the $C_1$ position of ribose is the initial site of attachment in the reaction mechanism proposed in FIG. 7. In $NAD^+$, $C_1$ forms the glycosidic bond to nicotinamide. FIG. 7 shows a proposed catalytic mechanism for the production of O-acetyl-ADP ribose. Acetyl-lysine condenses directly with the oxo-carbenium cation, which resulted from the elimination of nicotinamide from $NAD^+$. A hydroxide ion then attacks this intermediate to form a tetravalent intermediate, which can collapse to produce 1-O-acetyl-ADP ribose (Compound I, FIG. 7). The 1-O-acetyl-ADP ribose may then be attacked by the adjacent 2' OH group (via enzyme-assisted general base catalysis) to produce the 2-O-acetyl-ADP ribose (Compound II, FIG. 7). Once in bulk solution, the 2-O-acetyl-ADP ribose appears to be in rapid equilibrium with its solution migration adduct 3-O-acetyl-ADP ribose (Compound III, FIG. 7). Addition quantitative HPLC analysis followed by 2-dimentional NMR (heteronuclear multiple bond correlation) experiments have revealed the migration and equilibrium among the O-acetyl ADP ribose adducts depicted in FIG. 7. Searches of chemical data-bases for O-acetyl-ADP ribose produced no matches, indicating that it is a novel compound produced by a novel enzymatic reaction.

While not wishing to be bound to any particular molecular theory, we propose the possible chemical mechanism for catalysis by the SIR2 family (as depicted in FIG. 7). It is well-established that many NAD-dependent enzymes ($NAD^+$ glycohydrolases, ribosyl transferases and ADP-ribosyl cyclases) form a putative oxo-carbenium ADP-ribose cation as the direct product of nicotinamide elimination (14-16). Given this precedent for oxo-carbenium cation formation and the previously observed $NAD^+$:nicotinamide exchange reaction (7), SIR2 enzymes will likely form a similar intermediate. Interestingly, in the case of the SIR2 enzymes, oxo-carbenium cation formation appears to require acetyl-lysine binding (and/or deacetylation). Only in the presence of acetyl-lysine and $NAD^+$, can exogenously added nicotinamide exchange with the enzyme intermediate to reform $NAD^+$ (7).

Given our findings, it appears that the previously reported histone/protein ADP-ribosyltransferase activity (9-11) is a low efficiency side reaction that can be explained through the partial uncoupling of the intrinsic deacetylation/acetate ADP-ribosylation reactions. The fact that these enzymes are capable of an $NAD^+$-nicotinamide exchange reaction suggests that the oxo-carbenium cation of ADP ribose is at least partially susceptible to attack by the base nucleophile. However, the proposed oxo-carbenium cation of SIR2 enzymes appears to be exquisitely constructed to limit other possible side-reactions, such as attack by $H_2O$ or by nucleophilic amino-acid side chains, which would result in ADP ribose or protein ADP-ribosylation, respectively. We observed, at most, protein ADP-ribosylation that is ~0.1% of the authentic reaction described in this study. Also, ADP ribose was not detected as a primary enzymatic product. It may be possible that some uncoupling of this reaction to yield protein ADP-ribosylation could result from perturbations in native protein structure (partially unfolded protein, mutagenesis, inappropriate reaction conditions), and from extremely high concentrations of an alternate acceptor, such as reactive protein side-chains.

Why do the SIR2 enzymes go to great lengths to couple histone/protein deacetylation to the formation of O-acetyl-ADP ribose? It is attractive to propose that this novel molecule has a unique cellular function(s) that may be linked to SIR2's gene silencing effects. This implicates O-acetyl-ADP ribose as an important signaling molecule in biochemical pathways in which other enzymes/proteins may utilize O-acetyl-ADP ribose to elicit the proper cellular response. Such targets might include ATP-dependent chromatin remodeling enzymes, histone/protein acetyltransferases or poly (ADP-ribosyl)transferases. It is interesting to note that poly (ADP-ribosyl)transferases utilize $NAD^+$ to poly(ADP-ribosyl)ate proteins involved in the metabolism of nucleic acids and in the maintenance of chromatin architecture (15, 17). One intriguing possibility is that O-acetyl-ADP ribose could bind poly(ADP-ribosyl)transferases and block poly (ADP-ribosyl)ation. Moreover, $NAD^+$ levels in cells is inversely affected by the level of protein poly(ADP-ribosyl) ation (15, 17). Since poly(ADP-ribosyl)transferases and SIR2 enzymes exhibit similar $K_m$ values (~50-70 µM) for $NAD^+$, they may compete for the available $NAD^+$ and oppose each another's function. Recently, the observation that caloric restriction leading to increased life-span appears to be linked through an $NAD^+$ and SIR2-dependent pathway (18), raises the possibility that O-acetyl-ADP ribose may play a role in this phenomenon. It is important to note that bacteria do not have histones and yet they do have SIR2-like proteins with similar activity as has been shown here for HST2/SIR2/CobB/hSIRT2. Thus, histones need not be the only substrates for deacetylation by these enzymes. Identification of the authentic products and the catalytic mechanism of the SIR2-like enzymes has provided the initial basis for understanding the cellular role(s) played by this important family of proteins.

EXAMPLE II

Figure 8A:
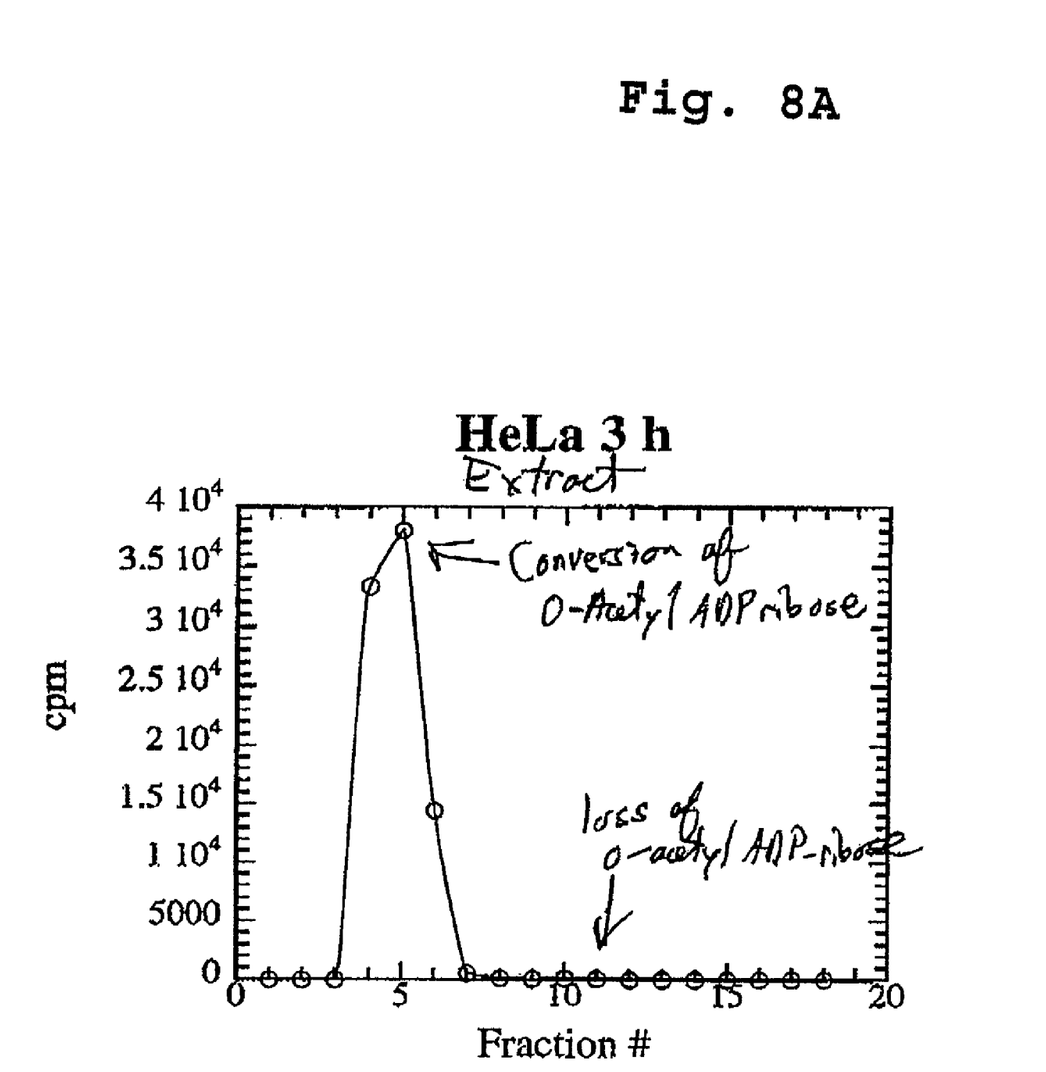
FIGS. 8A and 8B are graphs which clearly demonstrate that proteins present in a human cell extract convert O-acetyl-ADP ribose to a distinct, but as yet unidentified species. These findings implicate O-acetyl-ADP ribose as a second messenger, where additional proteins/enzymes are capable of terminating the signal through the enzymatic decomposition of O-acetyl-ADP ribose. These data also provide evidence for the existence of proteins/enzymes that bind/utilize O-acetyl-ADP ribose.
Figure 8B:
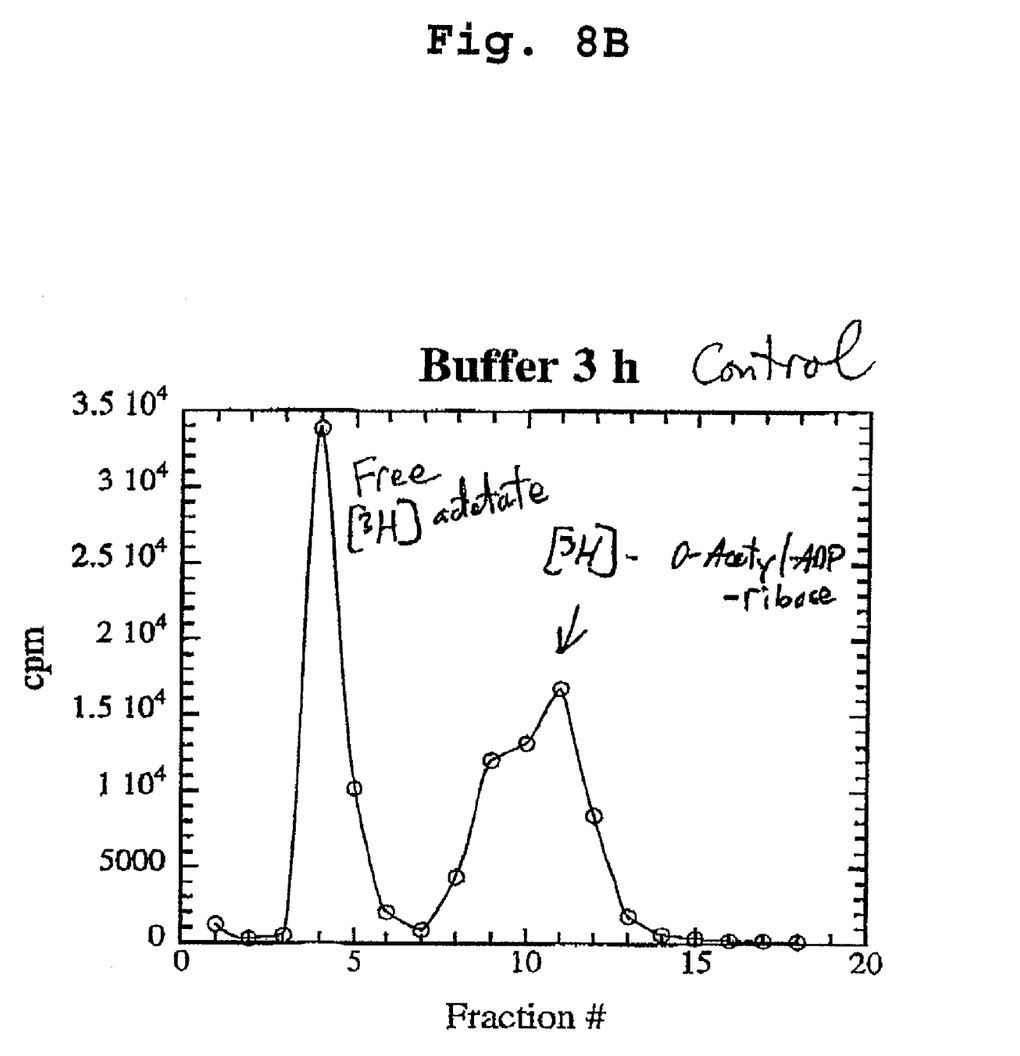

To provide evidence for the existence of human cellular proteins/enzymes that are capable of binding and catalyzing the conversion or decomposition of O-acetyl-ADP ribose, human HeLa cell extracts were generated and the ability of proteins within the extract to catalyze the decomposition of O-acetyl-ADP ribose was assessed. Radio-labeled O-acetyl-ADP ribose was generated and purified as described above, and was added to the HeLa cell extract. As a control, O-acetyl- ADP ribose was added to a buffer control. At time points up to 3 hrs, the samples were analyzed for the amount of O-acetyl-ADP ribose remaining (by HPLC as described above). The results, shown in FIGS. 8A and 8B clearly demonstrate the ability of the human cell extract to convert O-acetyl-ADP ribose to a distinct, but as yet unidentified species. These findings suggest that O-acetyl-ADP ribose could be acting as a second messenger, where additional proteins/enzymes are capable of terminating the signal through the enzymatic decomposition of O-acetyl-ADP ribose. These data also provide evidence for the existence of proteins/enzymes that bind/utilize O-acetyl-ADP ribose.

Enzymatic Generation of Novel O-acetyl-nucleotide Analogs

We have demonstrated that different nucleotide analogs, such as Nicotinamide Guanine Dinucleotide (NGD), can serve as substrates for the SIR2 family of enzymes, generating the novel O-acetyl-NDP ribose product. The details of the reaction conditions are as described in the materials and methods section. This enzymatic process may be used to advantage to generate novel O-acetyl-nucleotide analogs. These analogs may be used in the development of inhibitors for SIR2 and SIR homologs, or for the proteins/enzymes that normally bind/utilize O-acetyl-ADP ribose. More importantly, these enzyme-derived nucleotide analogs may serve as potent therapeutics for cancer and aging, releasing the block for transcriptionally-silenced genes that have been inappropriately silenced during tumorigenesis and aging, as discussed earlier.

Methods for Enzymatic Generation of Novel O-acetyl-nucleotide Analogs

Typical HST2 steady-state reactions to monitor deacetylation of AcLys-14 H3 peptide or nicotinamide formation with nicotinamide guanine dinucleotide (NGD) as an alternative substrate to NAD were carried out at various concentrations of AcLys-14 H3 peptide (5-100 µM) and NGD (10-400 µM). During the linear portion of the initial velocity, the reactions were monitored by reverse phase HPLC analysis on a Beckman Ultrasphere column (4.6 mm×15 cm). Samples were injected in 0.05% trifluoroacetic acid (TFA)/H$_2$O for 1 min before a linear gradient of 0-40% acetonitrile in 1-41 min.

EXAMPLE III

The data presented in the previous examples indicates that O-acetyl ADP ribose is a novel molecule demonstrating unique cellular function(s) that may be linked to SIR2's gene silencing or other physiological effects. It appears that O-acetyl-ADP ribose has an important signaling role in which other enzymes/proteins utilize O-acetyl-ADP ribose to elicit the proper cellular response. Such targets might include ATP-dependent chromatin remodeling enzymes, histone/protein acetyltransferases or poly(ADP-ribosyl)transferases. Also, the observation that caloric restriction leading to increased life-span appears to be linked through an NAD$^+$ and SIR2-dependent pathway, raises the possibility that O-acetyl-ADP ribose may play a role in this phenomenon.

To explore the function of SIR2-like enzymes and of O-acetyl-ADP ribose, microinjection analyses in living cells were performed which have provided evidence for phenotypic effects caused by SIR2- or O-acetyl-ADP ribose. The evidence presented herein suggests that cellular enzymes that metabolize/convert O-acetyl-ADP ribose are important in maintaining cell cycle control.

Micro-injection assays were performed in starfish and sea urchin ooctyes. Historically echinoderm development has been a biochemically tractable and well-defined system to assess biological function of prutiens, bio-active compounds and for detailed analyses of the cell cycle. This system is attractive for its amenability to quantitative microinjection assays, cell cycle analyses, biochemical fractionation and microscopic imaging of eggs and early embryos. Initially, we hypothesized that if O-acetyl-ADP ribose produced by SIR2 was involved in SIR2's gene silencing ability, then microinjection of O-acetyl-ADP ribose into a maturing oocyte should give rise to a phenotypic effect on the developing animal, perhaps through perturbations in normal gene expression patterns. Immature oocytes were micro-injected with HPLC-purified O-acetyl-ADP ribose or with a buffer control. The oocytes were allowed to mature by the addition of 1-methyladenine and assessed for developmental alterations.

Figure 9A:
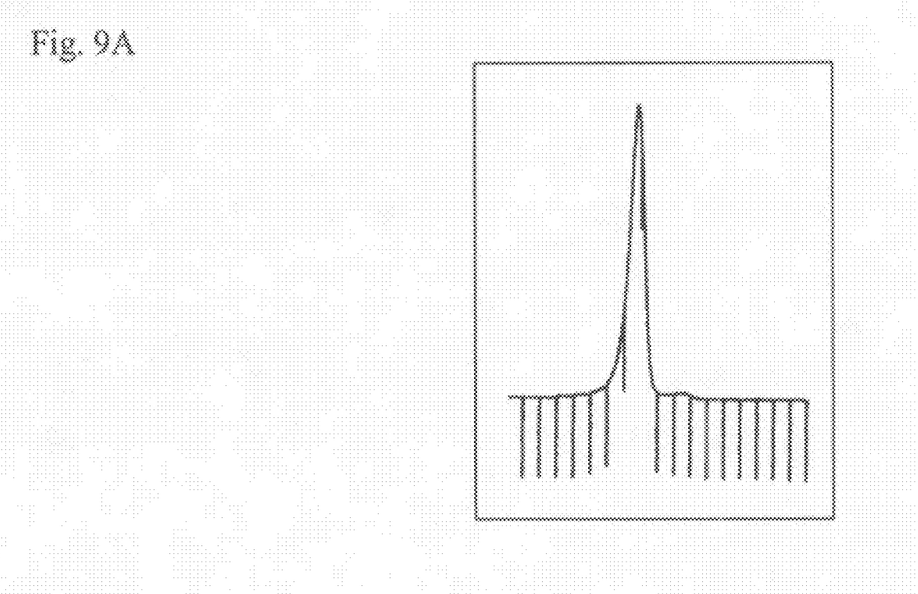
FIGS. 9A-9C are an elution trace and a pair of micrographs.
Figure 9B:
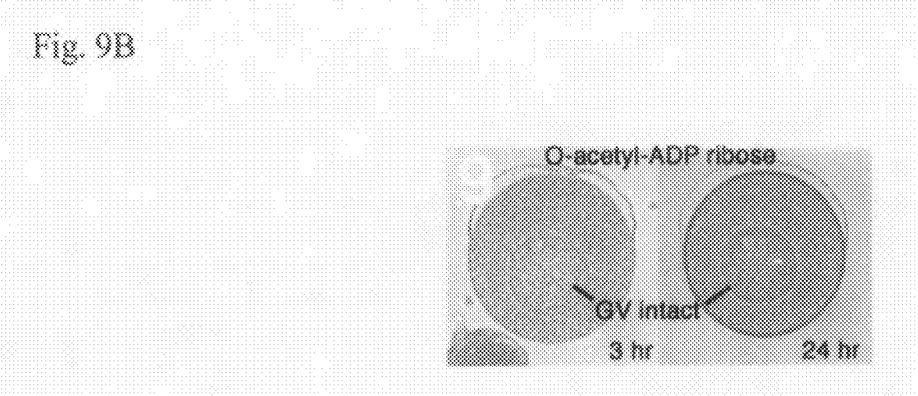
Figure 9C:
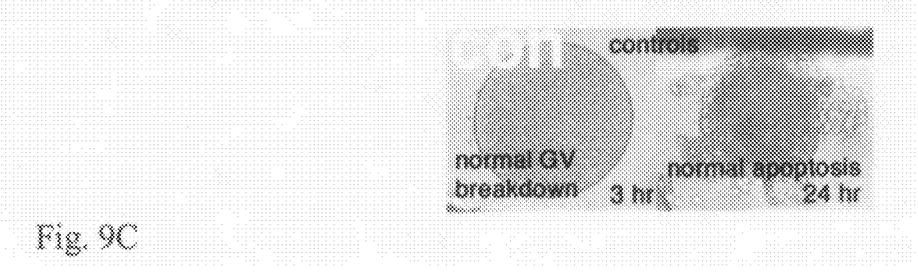

Compared to control injections, oocytes injected with O-acetyl-ADP ribose exhibited a delay in germinal vesicle breakdown (GVBD), or a complete block in oocyte maturation as assessed by GVBD and polar body extrusion. See FIG. 9 and Table I below. The dose-dependency indicated that below 0.32 mM no effect was observed. Given the amounts of O-acetyl-ADP ribose required for these phenotypes, we suspected that the injected O-acetyl-ADP ribose might be metabolized over time, resulting in a loss of the compound during the 24 hours of the assay. Supporting this assertion, we have demonstrated that HeLa cell extracts are capable of consuming O-acetyl ADP ribose, relative to a buffer control. See Example II. Together these data suggest the existence of enzymes that metabolize O-acetyl ADP ribose.

To complement these studies, we micro-injected active yeast HST2 and human SIR2 enzymes instead of O-acetyl-ADP ribose. We hypothesized that if acetylated protein substrates were available in the oocyte, then micro-injected enzyme would provide a more constant source of O-acetyl-ADP ribose. As a control, a catalytically impaired mutant of HST2 (R45A) was employed to ensure that any effects were due to the catalytic activity of the enzyme. The R45A mutant is >50-fold lower in catalytic efficiency ($k_{cat}$ and $k_{cat}/K_m$ for acetyl-peptide) compared to wild type enzyme (unpublished data).

TABLE I

Effects of O-acetyl ADP ribose on starfish oocyte maturation.

| Injected compound conc. in cytoplasm O-Ac ADP ribose | no effect | 1-2 hr delay | compete block | immediate death |
|---|---|---|---|---|
| 10 mg/ml (16 mM) | | | | 2/2 |
| 3.0 mg/ml (5 mM) | 2/3 | | | 1/3 |
| 1.7 mg/ml (3 mM) | | | 6/6 | |
| 1.0 mg/ml (1.6 mM) | | 1/23 | 22/23 | |
| 0.5 mg/ml (0.8 mM) | | 10/16 | 6/16 | |
| 0.2 mg/ml (0.32 mM) | 7/8 | | 1/8 | |
| 0.1 mg/ml (0.16 mM) | 16/16 | | | |
| 0.01 mg/ml (0.016 mM) | 8/8 | | | |

*Asterina miniata* immature oocytes were microinjected with the amounts of O-acetyl ADP ribose in PBS. The maturation hormone 1-methyladenine was added (10 µM) 25-30 minutes post-injection. Oocytes were monitored for GVBD and polar body extrusion. Non-injected and control injected oocytes showed synchronous GVBD within 35-45 minutes (depending on the batch). The number of oocytes per treatment is given. Combined results of 3 separate experiments (3 batches of O-acetyl ADP ribose).

Figure 10A:
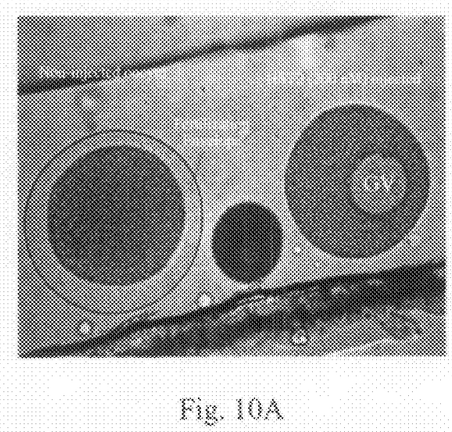
FIGS. 10A-C show HST2 micro-injection analysis of oocyte development.
Figure 10B:
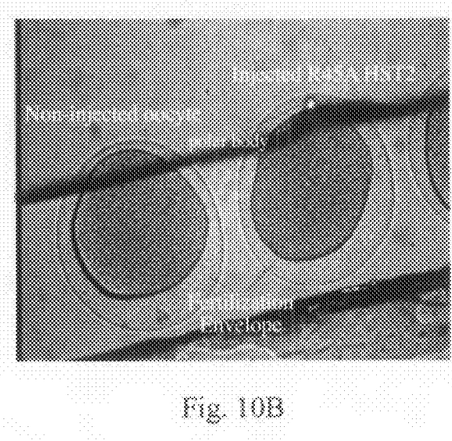
Figure 10C:
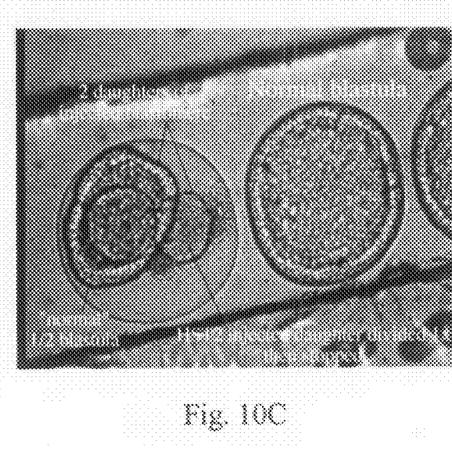

First, effects of HST2 (wild type and mutant) and human SIRT2 enzymes on sea star oocyte maturation were assessed. See Table II below. *Asterina miniata* immature oocytes were microinjected with the given enzymes in PBS. The maturation hormone 1-methyladenine was added (10 μM) 25-30 minutes post-injection. Oocytes were monitored for GVBD and polar body extrusion. Non-injected and control injected oocytes showed synchronous GVBD within 35-45 minutes (depending on the batch). A dosage response analysis was performed using final enzyme concentrations that ranged between 25-200 nM. Above 72 nM, both hSIRT2 and HST2 caused a complete block in maturation (no GVBD or polar body extrusion). At 60 nM, both enzymes caused a 2 hr delay in GVBD and polar body extrusion. With 25 nM hSIRT2 or HST2, no effect was observed. The catalytic mutant R45A displayed no observed effects at any concentration from 25-200 nM. Representative oocyte images are shown in the FIGS. 10A-10C. These data indicate a clear dosage dependence with the active enzymes, and suggest that hSIRT2 and HST2 are involved in a highly specific block in oocyte maturation.

TABLE II

Effects of yeast HST2 and human SIRT2 enzymes on sea star oocyte maturation.

| Enzyme | Final conc (nM) | n | Effects/Notes |
|---|---|---|---|
| HST2 | 25 | 10 | no observed effect |
| (2 preps) | 60 | 5 | 2 hr delay in GVBD |
| | 72 | 22 | complete block |
| | 200 | 10 | complete block in 9/10; 3 hr delay 1/10 |
| HST2 R45A | 25 | 5 | no observed effect |
| | 60 | 5 | no observed effect |
| | 72 | 13 | no observed effect |
| | 200 | 5 | no observed effect |
| hSIRT2 | 25 | 5 | no observed effect |
| (1 prep) | 60 | 5 | 2 hr delay in GVBD and polar body extrusion |
| | 200 | 5 | complete block |

*Asterina miniata* immature oocytes were microinjected with the given enzymes in PBS. The maturation hormone 1-methyladenine was added (10 μM) 25-30 minutes post-injection. Oocytes were monitored for GVBD and polar body extrusion. Non-injected and control injected oocytes showed synchronous GVBD within 35-45 minutes (depending on the batch). The number of oocytes per treatment (n) is given. Data are from four separate batches of oocytes. All oocytes for a given treatment responded in the same way unless indicated otherwise (e.g. see 200 nM HST2 injection).

To examine whether these SIR2 enzymes caused any phenotypic effects on early embryonic cell division, HST2 or the R45A mutant were micro-injected into one cell of the two-cell stage embryos. *Asterina miniata* oocytes were matured by addition of the hormone 1-methyladenine and then fertilized. One cell zygotes were then placed in injection chambers. After the first cell division, one daughter blastomere was microinjected with the indicated enzyme (see table and figure below). Embryos were monitored for further cell divisions over time. The non-injected daughter blastomere served as the internal control in each experiment. At and above 72 nM, HST2 caused a complete block in cell division either at the next or subsequent division, while the non-injected daughter blastomere developed normally. Additionally, cells that did make it through the next division displayed a slight delay before a complete block in the next round. Most cells injected at the lower 25 nM HST2 developed normally. The R45A mutant exhibited no phenotype at any concentration. Again, there was a clear dosage effect that paralleled the effect observed on oocyte maturation. Given the low concentrations necessary for the blocks, the dosage effects, and the requirement for active enzyme, collectively suggest that these SIR2 enzymes are causing a specific and highly potent cell cycle block.

TABLE III

Effects of HST2 on early embryonic cell division.

| Enzyme | Final conc (nM) in blastomere | n | Effects: Next cell division | Effects: $3^{rd}$ cell division | Effects: other |
|---|---|---|---|---|---|
| HST2 (2 preps) | 25 | 5 | 4/5 normal 1/5 as slight delay | Normal Normal | Normal developm Normal developm |
| HST2 (2 preps) | 72 | 10 | 4/10 slight delay 6/10 no division (complete block) | Complete block | — |
| HST2 (2 preps) | 200 | 7 | 2/7 slight delay 5/7 no division (complete block) | Complete block | — |
| HST2 R45A | 25 | 5 | Normal | Normal | Normal developm |
| HST2 R45A | 72 | 3 | Normal | Normal | Normal developm |
| HST2 R45A | 200 | 5 | normal | Normal | Normal developm |

*Asterina miniata* oocytes were matured by addition of the hormone 1-methyladenine and then fertilized. One cell zygotes were then placed in injection chambers. After the first cell division, one daughter blastomere was microinjected with the indicated enzyme. Embryos were monitored for further cell divisions over time. The non-injected daughter blastomere served as the internal control in each experiment. The number of injected embryos per treatment is given (n). Data are from two separate batches of oocytes.

Quite strikingly, injection of pure O-acetyl ADP ribose mimicked the oocyte maturation block that was observed when low nM levels of active enzyme were injected. Not only did O-acetyl ADP ribose block oocyte maturation, but it also delayed apoptosis that normally occurs after ~24 hrs if the oocyte is not fertilized. Both SIR2 enzymes and O-acetyl ADP ribose appear to have an effect on oocyte longevity in this context. The results provide additional biological/biochemical data that indicate the product O-acetyl ADP ribose plays an integral, if not sufficient role in SIR2-dependent phenotypic alterations. The anti-aging phenotypes and the cell-cycle blot suggest the importance of our initial discovery (unique reaction of SIR2-family enzymes and the production of O-acetyl ADP ribose) further supports the ramifications of O-acetyl ADP ribose and it's analogs as potential cancer therapeutics or anti-aging drugs.

REFERENCES

1. Frye, R. A. (2000) *Biochem Biophys Res Commun* 273, 793-8.
2. Loo, S. & Rine, J. (1995) *Annu Rev Cell Dev Biol* 11, 519-48.
3. Gottlieb, S. & Esposito, R. E. (1989) *Cell* 56, 771-6.
4. Guarente, L. (1999) *Nat Genet* 23, 281-5.

5. Brachmann, C. B., Sherman, J. M., Devine, S. E., Cameron, E. E., Pillus, L. & Boeke, J. D. (1995) *Genes Dev* 9, 2888-902.
6. Tsang, A. W. & Escalante-Semerena, J. C. (1998) *J Biol Chem* 273, 31788-94.
7. Landry, J., Sutton, A., Tafrov, S. T., Heller, R. C., Stebbins, J., Pillus, L. & Sternglanz, R. (2000) *Proc Natl Acad Sci USA* 97, 5807-11.
8. Smith, J. S., Brachmann, C. B., Celic, I., Kenna, M. A., Muhammad, S., Starai, V. J., Avalos, J. L., Escalante-Semerena, J. C., Grubmeyer, C., Wolberger, C. & Boeke, J. D. (2000) *Proc Natl Acad Sci USA* 97, 6658-63.
9. Tanny, J. C., Dowd, G. J., Huang, J., Hilz, H. & Moazed, D. (1999) *Cell* 99, 735-45.
10. Imai, S., Armstrong, C. M., Kaeberlein, M. & Guarente, L. (2000) *Nature* 403, 795-800.
11. Frye, R. A. (1999) *Biochem Biophys Res Commun* 260, 273-9.
12. Tanner, K. G., Langer, M. R. & Denu, J. M. (2000) *Biochemistry* in press.
13. Annan, R. S. & Carr, S. A. (1996) *Anal Chem* 68, 3413-21.
14. Scheuring, J. & Schramm, V. L. (1997) *Biochemistry* 36, 8215-23.
15. Ziegler, M. (2000) *Eur J Biochem* 267, 1550-64.
16. Cakir, K.-S. C., Muller-Steffner, H. & Schuber, F. (2000) *Biochem J* 349, 203-210.
17. D'Amours, D., Desnoyers, S., D'Silva, I. & Poirier, G. G. (1999) *Biochem J* 342, 249-68.
18. Lin, S. J., Defossez, P. A. & Guarente, L. (2000) *Science* 289, 2126-8.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A nucleotide analog of O-acetyl ADP ribose, wherein said nucleotide analog is O-acetyl-nucleoside diphosphate (NDP) ribose.

2. The nucleotide analog of claim 1, wherein said nucleoside diphosphate comprises a purine.

3. The nucleotide analog of claim 2, wherein said purine is guanine.

4. The nucleotide analog of claim 1, wherein said nucleoside diphosphate comprises a pyrimidine.

5. The nucleotide analog of claim 1, wherein said analog is non-hydrolyzable.

6. The nucleotide analog of claim 1, further comprising a detectable label.

7. The nucleotide analog of claim 6, wherein said detectable label is selected from the group consisting of fluorescein, rhodamine, radioactive isotopes, and chemiluminescence labels.

* * * * *